Dec. 18, 1962 M. F. DE MOTT ETAL Plant Pat. 2,201
ROSE PLANT
Filed Oct. 16, 1961
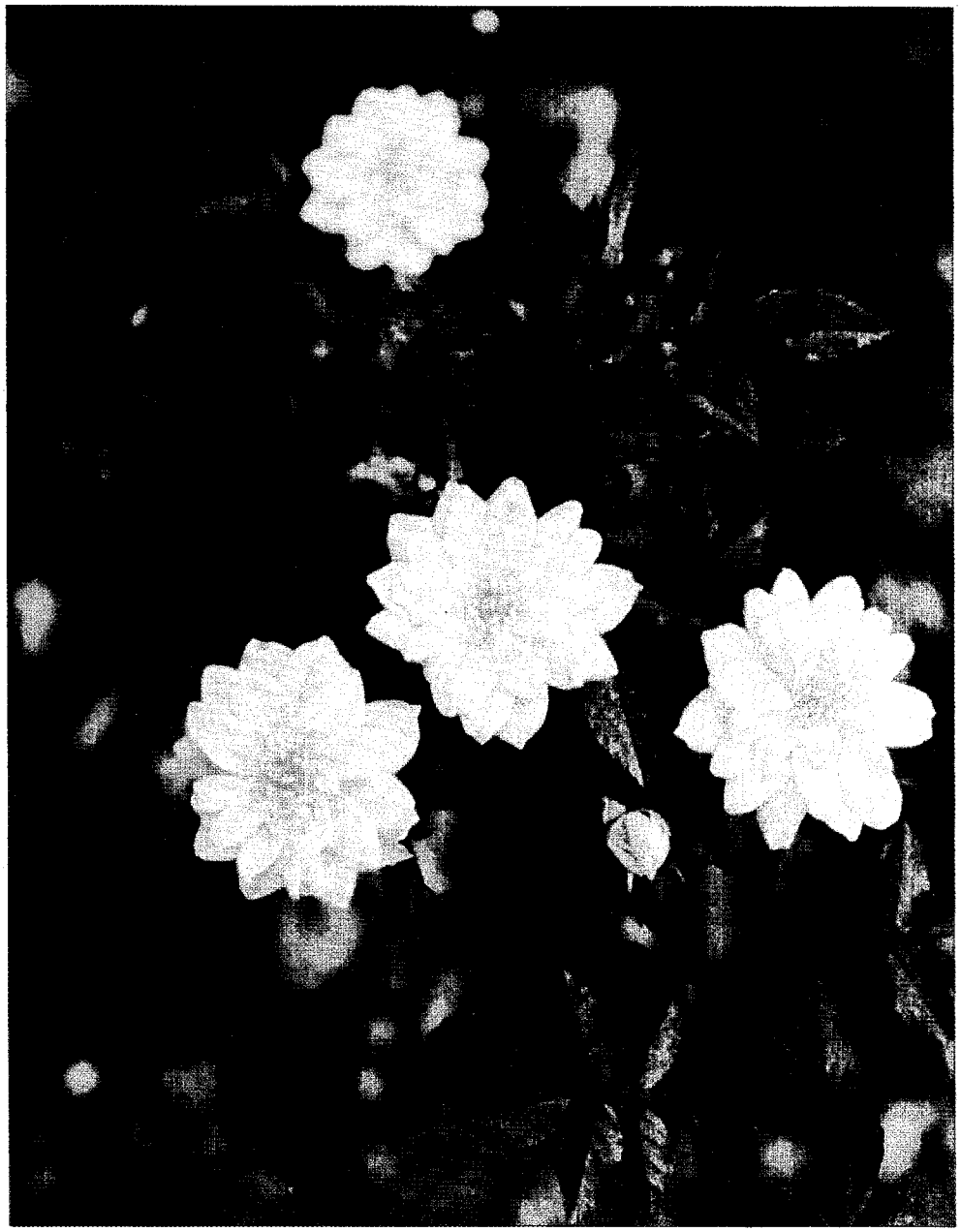
Monroe F. DeMott
George E. Johnson, INVENTORS.
BY Clarence A. O'Brien and Harvey B. Jacobson
Attorneys United States Patent Office Plant Pat. 2,201
Patented Dec. 18, 1962

2,201
ROSE PLANT

Monroe F. De Mott and George E. Johnson,
both of Clinton, N.J.

Filed Oct. 16, 1961, Ser. No. 145,522
1 Claim. (Cl. 47—61)

The present discovery relates to a new and distinct rose plant. This variety is a sport of the rose plant "Peace" (U.S. Plant Patent No. 591).

Asexual reproduction of our new variety at Clinton, New Jersey, for a period of two years has proven that the characteristics thereof are firmly fixed. This new variety is a miniature of the parent variety, yet has more blossoms and blooms more freely. A further characteristic of this variety over its parent is its better resistance to mildew. The variety, grown in the same bed with other miniatures, was the last to show any sign of mildew.

This miniature of the renowned "Peace" has all the good points of its parent to which is added its ability to withstand temperatures well below zero. Its free blooming habit, its resistance to mildew and its strong growth while still maintaining its miniature size all combine to make it an outstanding miniature rose.

Our new variety has been asexually reproduced at Clinton, New Jersey, by rooting cuttings.

In the drawing forming part hereof there is disclosed the full blooming flower and foliage of our new variety.

The characteristics of this variety are as follows, with color references of ordinary dictionary meaning.

*Plant*

Growth: Makes many breaks after starting. Practically every cutting responds to growth.
Blooming habits: Very free.
Disease resistance: Very healthy and resistant to mildew.
*Stem*: Miniature in size but strong and sturdy. Smooth with very few thorns. Eyes are close together, making this miniature rose an excellent flowering variety.
Foliage:
*Quantity*.—Abundant.

*Type*.—Mostly five leaflets.
*Color*.—Ivy green, slightly lighter on under side.
*Texture*.—Clean and very smooth.
*Leaf stems*.—Short, many breaks, miniature pointed.
*Shape*.—Long.
*Size*.—Typical of miniature.

*Flower*

Bud:
*Color*.—Ivory yellow, pink tipped.
*Size*.—Approximately ⅛" x ¼".
*Form*.—Urn-shaped.
*Peduncle*.—Very strong, holding flowers upright—no weak necks. Same color as stems.
*Calyx*.—Narrow and branched.
Flower:
*Form*.—High centered and opens in spiral pattern. Petals open flat and hold their rose form until petals drop.
*Color*.—Identical in color to the parent variety—ivory yellow, pink tipped, becoming more pronounced in cooler weather.
*Size*.—Diameter ½" to 1" about ⅓" depth.
*Fragrance*.—Light.
*Petalage*.—50 to 55.
*Longevity*.—Very long since petals rarely drop.
Petals:
*Texture*.—Firm yet soft.
*Shape*.—Outer petals oval shaped, slightly pointed. Petals rarely turn back but generally open flat when in the last stages of bloom.
*Size*.—Average ⅜", center petals smaller.
Reproductive organs: Pistils and stamens visible as flower opens. Pistils are yellow.

Having thus disclosed the invention, we claim:

A new and distinct variety of rose plant, substantially as herein shown and described, originating as a sport of Peace (U.S. Plant Patent No. 591), characterized as to novelty by its miniature size, profuse and free blooming habit and resistance to mildew.

No references cited.